United States Patent
Christiansen

(10) Patent No.: US 12,371,609 B2
(45) Date of Patent: Jul. 29, 2025

(54) ANODICALLY-COLORING ELECTROCHROMIC COMPOUNDS, AND DEVICES AND COMPOSITIONS CONTAINING SAME

(71) Applicant: Vitro Flat Glass LLC, Cheswick, PA (US)

(72) Inventor: Dylan Christiansen, Pittsburgh, PA (US)

(73) Assignee: Vitro Flat Glass LLC, Cheswick, PA (US)

( * ) Notice: Subject to any disclaimer, the term of this patent is extended or adjusted under 35 U.S.C. 154(b) by 679 days.

(21) Appl. No.: 17/826,230

(22) Filed: May 27, 2022

(65) Prior Publication Data

US 2022/0389307 A1 Dec. 8, 2022

Related U.S. Application Data

(60) Provisional application No. 63/194,303, filed on May 28, 2021.

(51) Int. Cl.
 *C09K 9/02* (2006.01)
 *C07D 495/04* (2006.01)
 (Continued)

(52) U.S. Cl.
 CPC .............. *C09K 9/02* (2013.01); *C07D 495/04* (2013.01); *G02F 1/1514* (2019.01); *G02F 1/155* (2013.01); *C09K 2211/1018* (2013.01)

(58) Field of Classification Search
 CPC .......................... C09K 9/02; C09K 2211/1018; C07D 495/04; G02F 1/155; G02F 1/1514
 See application file for complete search history.

(56) References Cited

U.S. PATENT DOCUMENTS

| | | |
|---|---|---|
| 2019/0218338 A1 | 7/2019 | Reynolds et al. |
| 2020/0393732 A1 | 12/2020 | Reynolds et al. |
| 2022/0390805 A1* | 12/2022 | Maslov ................. G02F 1/1516 |

FOREIGN PATENT DOCUMENTS

| | | | |
|---|---|---|---|
| WO | WO2020262443 A1 * | 12/2020 | ........... C07D 495/04 |
| WO | 2021075999 A1 | 4/2021 | |

OTHER PUBLICATIONS

Mathieu Turbiez, Djibril Faye, Philippe Leriche and Pierre Frere,Bis-EDOT end capped by n-hexyl or n-hexylsulfanyl groups: the effect of the substituents on the stability of the oxidized states, New J. Chem., 2015, 39, 1678-4684. (Year: 2015).*

(Continued)

*Primary Examiner* — Bijan Ahvazi
(74) *Attorney, Agent, or Firm* — The Webb Law Firm

(57) ABSTRACT

The present invention relates to an anodically-coloring electrochromic compound represented by the following Formula (I),

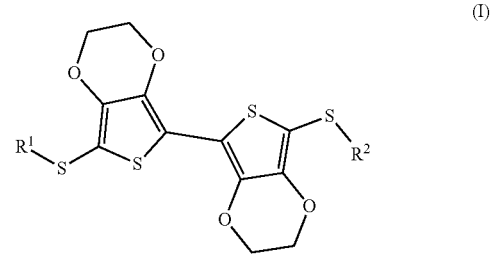

With reference to Formula (I), $R^1$ and $R^2$ are each independently selected from linear or branched $C_3$-$C_{20}$ alkyl. The present invention also relates to electrochromic devices and (Continued)

compositions that include an anodically-coloring electrochromic compound represented by Formula (I).

19 Claims, 2 Drawing Sheets

(51) Int. Cl.
*G02F 1/1514* (2019.01)
*G02F 1/155* (2006.01)

(56) References Cited

OTHER PUBLICATIONS

Christiansen et al., "Color Control in Cathodically Coloring and Anodically Coloring Conjugated Organic Electrochromics", MRS Symposium Presentation, 2017, pp. 1-24.
Christiansen et al., "Electrochromism of alkylene-linked discrete chromophore polymers with broad radical cation light absorption", Polym. Chem., 2018, pp. 1-12.
Christiansen, "Pigments of My Imagination: Controlling Color and Redox Properties of Conjugated Organic Electrochromic Materials", Dissertation Presented to the Academic Faculty, 2019, pp. 1-205.
Lin et al., "Structural, Optical, and Electronic Properties of a Series of 3,4-Propylenedioxythiophene Oligomers in Neutral and Various Oxidation States", J. Am. Chem. Soc., 2011, pp. 11339-11350, vol. 133.
Nishinga et al., "Stable Radical Cations and their π-Dimers Prepared from Ethylene- and Propylene-3,4-dioxythiophene Co-oligomers: Combined Experimental and Theoretical Investigations", J. Org. Chem., 2017, pp. 7245-7253, vol. 82.
Turbiez et al., "Bis-EDOT end capped by n-hexyl or n-hexylsulfanyl groups: the effect of the substituents on the stability of the oxidized states", New Journal of Chemistry, 2015, pp. 1678-1684, vol. 39, No. 3.

\* cited by examiner

ANODICALLY-COLORING ELECTROCHROMIC COMPOUNDS, AND DEVICES AND COMPOSITIONS CONTAINING SAME

CROSS REFERENCE TO RELATED APPLICATION

The present application is entitled to and claims priority to U.S. Provisional Patent Application No. 63/194,303, filed on 28 May 2021, the disclosure of which is incorporated herein by reference in its entirety.

FIELD

The present invention relates to anodically-coloring electrochromic compounds, and electrochromic devices and compositions containing such anodically-coloring electrochromic compounds.

BACKGROUND

Electrochromism involves a reversible change in a material's visible color and/or transmittance of visible light with the application of an electrical potential. The change in color and/or transmittance typically involves alternately cycled oxidized and reduced charge states. Generally, a material the generates a color while undergoing reduction is referred to as a cathodically-coloring electrochromic material; and a material that generates color while undergoing oxidation is referred to as an anodically-coloring electrochromic material.

Anodically-coloring electrochromic materials in some instances, are desirably colorless in the neutral state, and provide an advantageous degree of color reproducibility and contrast. In some instances, anodically-coloring electrochromic materials, in the neutral and/or radical cation states, can have inadequate solubility in liquid electrochromic compositions from which an electrochromic layer is prepared.

It would be desirable to develop new anodically-coloring electrochromic materials. It would be further desirable that such newly developed anodically-coloring electrochromic materials provide properties and performance that is at least as good as that of presently available anodically-coloring electrochromic materials.

SUMMARY

In accordance with the present invention, there is provided an electrochromic device comprising:
(a) a first substrate having a surface comprising a first transparent electrode layer;
(b) a second substrate having a surface comprising a second transparent electrode layer,
wherein said first transparent electrode layer and said second transparent electrode layer are in opposing spaced opposition; and
(c) an electrochromic layer interposed between said first transparent electrode layer and said second transparent electrode layer, wherein said electrochromic layer comprises,
(i) a cathodic component,
(ii) an anodic component,
(iii) an electrolyte, and
(iv) a polymer matrix, wherein said anodic component comprises an anodically-coloring electrochromic compound represented by the following Formula (I),

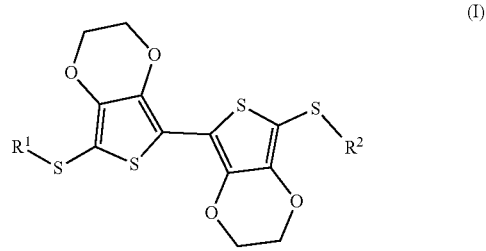

With reference to Formula (I), $R^1$ and $R^2$ are each independently selected from linear or branched $C_3$-$C_{20}$ alkyl.

In further accordance with the present invention there is provided an electrochromic composition comprising:
(i) a cathodic component,
(ii) an anodic component,
(iii) an electrolyte,
(iv) a polymeric thickener, and
(v) a solvent.

The anodic component of the electrochromic composition comprises an anodically-coloring electrochromic compound represented by Formula (I), as shown above, where $R^1$ and $R^2$ are each independently selected from linear or branched $C_3$-$C_{20}$ alkyl.

In further accordance with the present invention there is provided an anodically-coloring electrochromic compound represented by Formula (I), as shown above, where $R^1$ and $R^2$ are each independently selected from linear or branched $C_3$-$C_{20}$ alkyl.

The features that characterize the present invention are pointed out with particularity in the claims, which are annexed to and form a part of this disclosure. These and other features of the invention, its operating advantages and the specific objects obtained by its use will be more fully understood from the following detailed description in which non-limiting embodiments of the invention are illustrated and described.

BRIEF DESCRIPTION OF THE DRAWINGS

In FIGS. 1 and 2 like characters refer to the same components and/or elements, as the case may be, unless otherwise stated.

DETAILED DESCRIPTION

Figure 1:
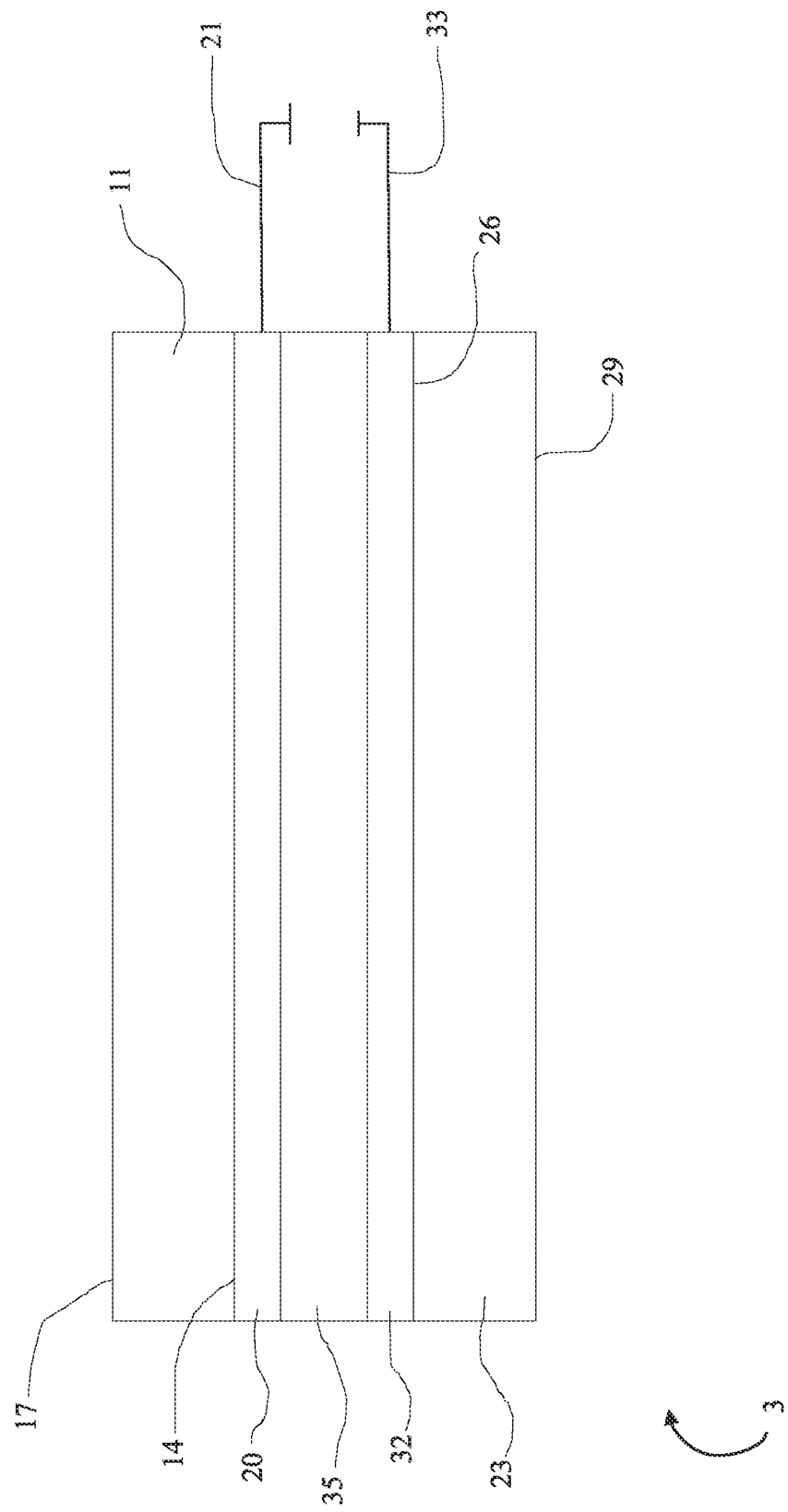
FIG. 1 is a representative side elevational sectional view of an electrochromic device according to the present invention.

As used herein, the articles "a," "an," and "the" include plural referents unless otherwise expressly and unequivocally limited to one referent.

Unless otherwise indicated, all ranges or ratios disclosed herein are to be understood to encompass any and all subranges or subratios subsumed therein. For example, a stated range or ratio of "1 to 10" should be considered to include any and all subranges between (and inclusive of) the minimum value of 1 and the maximum value of 10; that is, all subranges or subratios beginning with a minimum value of 1 or more and ending with a maximum value of 10 or less, such as but not limited to, 1 to 6.1, 3.5 to 7.8, and 5.5 to 10.

As used herein, unless otherwise indicated, left-to-right representations of linking groups, such as, divalent linking groups, are inclusive of other appropriate orientations, such as, but not limited to, right-to-left orientations. For purposes of non-limiting illustration, the left-to-right representation of the divalent linking group

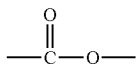

or equivalently —C(O)O—, is inclusive of the right-to-left representation thereof,

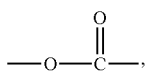

or equivalently —O(O)C— or —OC(O)—.

Other than in the operating examples, or where otherwise indicated, all numbers expressing quantities of ingredients, reaction conditions, and so forth used in the specification and claims are to be understood as modified in all instances by the term "about."

As used herein, molecular weight values of polymers, such as weight average molecular weights (Mw) and number average molecular weights (Mn), are determined by gel permeation chromatography using appropriate standards, such as, polystyrene standards.

As used herein, polydispersity index (PDI) values represent a ratio of the weight average molecular weight (Mw) to the number average molecular weight (Mn) of the polymer (i.e., Mw/Mn).

As used herein, the term "polymer" means homopolymers (e.g., prepared from a single monomer species), copolymers (e.g., prepared from at least two monomer species), and graft polymers.

As used herein, the term "(meth)acrylate" and similar terms, such as, "(meth)acrylic acid ester" means methacrylates and/or acrylates. As used herein, the term "(meth)acrylic acid" means methacrylic acid and/or acrylic acid.

The anodically-coloring electrochromic compounds/materials of the present invention are also referred to herein as anodically-coloring electrochromic bithieno-dioxine compounds/materials.

The anodically-coloring electrochromic compounds of the present invention, as described herein, including, but not limited to, anodically-coloring electrochromic compounds represented by Formula (I), can optionally further include one or more coproducts, resulting from the synthesis of such compounds.

As used herein, the term "electrochromic" and similar terms, such as, "electrochromic compound" means having an absorption spectrum for at least visible radiation that varies in response to the application of an electric potential. Further, as used herein the term "electrochromic material" means any substance that is adapted to display elecrochromic properties (such as, adapted to have an absorption spectrum for at least visible radiation that varies in response to an applied electric potential) and which includes at least one electrochromic compound.

As used herein, the term "electric potential" and related terms such as, "electrical potential" means an electric potential that is capable of causing a response in a material, such as, but not limited to, transforming an electrochromic material from one form or state to another, as will be discussed in further detail herein.

As used herein to modify the term "state," the terms "first" and "second" are not intended to refer to any particular order or chronology, but, instead refer to two different conditions or properties. For purposes of non-limiting illustration, the first state and the second state of an electrochromic compound, such as, an anodically-coloring electrochromic compound, can differ with respect to at least one optical property, such as, but not limited to, the absorption of visible and/or UV radiation. Thus, according to various non-limiting embodiments disclosed herein, the anodically-coloring electrochromic compounds of the present invention can have a different absorption spectrum in each of the first and second state. For example, while not limiting herein, an anodically-coloring electrochromic compound of the present invention can be clear in the first state and colored in the second state. Alternatively, an anodically-coloring electrochromic compound of the present invention can have a first color in the first state and a second color in the second state.

As used herein the term "display" means the visible or machine-readable representation of information in words, numbers, symbols, designs or drawings. Non-limiting examples of display elements include screens, monitors, and security elements, such as, security marks.

As used herein the term "window" means an aperture adapted to permit the transmission of radiation therethrough. Non-limiting examples of windows include automotive and aircraft transparencies, windshields, filters, shutters, and optical switches.

As used herein the term "mirror" means a surface that specularly reflects a large fraction of incident light.

As used herein, spatial or directional terms, such as, "left", "right", "inner", "outer", "above", "below", and the like, relate to the invention as it is depicted in the drawing figures. It is to be understood, however, that the invention can assume various alternative orientations and, accordingly, such terms are not to be considered as limiting.

As used herein, the terms "formed over," "deposited over," "provided over," "applied over," residing over," or "positioned over," mean formed, deposited, provided, applied, residing, or positioned on but, not necessarily in direct (or abutting) contact with the underlying element, or surface of the underlying element. For example, a layer "positioned over" a substrate does not preclude the presence of one or more other layers, coatings, or films of the same or different composition located between the positioned or formed layer and the substrate.

As used herein, the terms "interposed" and "interposed between," mean residing or positioned between, but, not necessarily in direct (or abutting) contact with overlying and/or underlying elements, or surfaces thereof. For example, a layer "interposed between" a first substrate and a second substrate does not preclude the presence of one or more other layers, coatings, or films of the same or different composition located between the interposed layer and the first and/or second substrates.

All documents, such as, but not limited to, issued patents and patent applications, referred to herein, and unless otherwise indicated, are to be considered to be "incorporated by reference" in their entirety.

As used herein, recitations of "linear or branched" groups, such as, linear or branched alkyl, are herein understood to include: a methylene group or a methyl group; groups that are linear, such as, linear $C_2$-$C_{20}$ alkyl groups; and groups that are appropriately branched, such as, branched $C_3$-$C_{20}$ alkyl groups.

The term "alkyl" as used herein means linear or branched, cyclic or acyclic $C_1$-$C_{25}$ alkyl. Linear or branched alkyl can include $C_1$-$C_{25}$ alkyl, such as $C_1$-$C_{20}$ alkyl, such as $C_2$-$C_{10}$ alkyl, such as, $C_1$-$C_{12}$ alkyl, such as, $C_1$-$C_6$ alkyl. Examples of alkyl groups from which the various alkyl groups of the present invention can be selected from, include, but are not limited to, those recited further herein. Alkyl groups can include "cycloalkyl" groups. The term "cycloalkyl" as used herein means groups that are appropriately cyclic, such as, but not limited to, $C_3$-$C_{12}$ cycloalkyl (including, but not limited to, cyclic $C_3$-$C_{10}$ alkyl, or cyclic $C_5$-$C_7$ alkyl) groups. Examples of cycloalkyl groups include, but are not limited to, those recited further herein. The term "cycloalkyl" as used herein also includes: bridged ring polycycloalkyl groups (or bridged ring polycyclic alkyl groups), such as, but not limited to, bicyclo[2.2.1]heptyl (or norbornyl) and bicyclo[2.2.2]octyl; and fused ring polycycloalkyl groups (or fused ring polycyclic alkyl groups), such as, but not limited to, octahydro-1H-indenyl, and decahydronaphthalenyl.

The term "heterocycloalkyl" as used herein means groups that are appropriately cyclic, such as, but not limited to, $C_2$-$C_{12}$ heterocycloalkyl groups, such as, $C_2$-$C_{10}$ heterocycloalkyl groups, such as $C_5$-$C_7$ heterocycloalkyl groups, and which have at least one hetero atom in the cyclic ring, such as, but not limited to, O, S, N, P, and combinations thereof. Examples of heterocycloalkyl groups include, but are not limited to, imidazolyl, tetrahydrofuranyl, tetrahydropyranyl and piperidinyl. The term "heterocycloalkyl" as used herein also includes: bridged ring polycyclic heterocycloalkyl groups, such as, but not limited to, 7-oxabicyclo[2.2.1]heptanyl; and fused ring polycyclic heterocycloalkyl groups, such as, but not limited to, octahydrocyclopenta[b]pyranyl, and octahydro-1H-isochromenyl.

As used herein, the term "aryl" and related terms, such as "aryl group", means an aromatic cyclic monovalent hydrocarbon radical. As used herein, the term "aromatic" and related terms, such as "aromatic group", means a cyclic conjugated hydrocarbon having stability (due to delocalization of pi-electrons) that is significantly greater than that of a hypothetical localized structure. Examples of aryl groups include $C_6$-$C_{14}$ aryl groups, such as, but not limited to, phenyl, naphthyl, phenanthryl, and anthracenyl.

The term "heteroaryl", as used herein, includes, but is not limited to, $C_3$-$C_{18}$ heteroaryl, such as, but not limited to, $C_3$-$C_{10}$ heteroaryl (including fused ring polycyclic heteroaryl groups) and means an aryl group having at least one hetero atom in the aromatic ring, or in at least one aromatic ring in the case of a fused ring polycyclic heteroaryl group. Examples of heteroaryl groups include, but are not limited to, furanyl, pyranyl, pyridinyl, quinolinyl, isoquinolinyl, and pyrimidinyl.

The term "aralkyl", as used herein, includes, but is not limited to, $C_6$-$C_{24}$ aralkyl, such as, but not limited to, $C_6$-$C_{10}$ aralkyl, and means an alkyl group substituted with an aryl group. Examples of aralkyl groups include, but are not limited to, benzyl and phenethyl.

Representative alkyl groups include, but are not limited to, methyl, ethyl, propyl, isopropyl, butyl, isobutyl, sec-butyl, tert-butyl, pentyl, neopentyl, hexyl, heptyl, octyl, nonyl and decyl. Representative alkenyl groups include, but are not limited to, vinyl, allyl, and propenyl. Representative alkynyl groups include, but are not limited to, ethynyl, 1-propynyl, 2-propynyl, 1-butynyl, and 2-butynyl. Representative cycloalkyl groups include, but are not limited to, cyclopropyl, cyclobutyl, cyclopentyl, cyclohexyl, and cyclooctyl.

The term "nitrogen-containing heterocycle", such as, "nitrogen-containing hererocycle group" or nitrogen-containing heterocycle substituent", as used herein, includes, but is not limited to, a nitrogen-containing ring in which the nitrogen-containing ring is bonded through a ring nitrogen. Examples of nitrogen-containing heterocycles include, but are not limited to, cyclic aminos, such as morpholino, piperidino, pyrrolidino, and decahydroisoquinolino; and heteroaromatics, such as imidazole, pyrrole, indole, and carbazole.

As used herein, recitations of "substituted" group, means a group including, but not limited to, alkyl group, heterocycloalkyl group, aryl group, and/or heteroaryl group, in which at least one hydrogen thereof has been replaced or substituted with a group or "substituent" that is other than hydrogen, such as, but not limited to: alkoxy groups; halo groups (e.g., F, Cl, I, and Br); hydroxyl groups; thiol groups; alkylthio groups; arylthio groups; ketone groups; aldehyde groups; carboxylic ester groups; carboxylic acid groups; phosphoric acid groups; phosphoric acid ester groups; sulfonic acid groups; sulfonic acid ester groups; nitro groups; cyano groups; alkyl groups; alkenyl groups; alkynyl groups; haloalkyl groups; perhaloalkyl groups; heterocycloalkyl groups; aryl groups (including alkaryl groups, including hydroxyl substituted aryl, such as, phenol, and including poly-fused-ring aryl); aralkyl groups; heteroaryl groups (including poly-fused-ring heteroaryl groups); amino groups, such as, —N($R^{11'}$)($R^{12'}$) where $R^{11'}$ and $R^{12'}$ are each independently selected from, for example, hydrogen, alkyl, heterocycloalkyl, aryl, or heteroaryl; carboxylate groups; siloxane groups; alkoxysilane groups; polysiloxane groups; amide groups; carbamate groups; carbonate groups; urea groups; trialkylsilyl groups; nitrogen-containing heterocycles; or combinations thereof, including those classes and examples as described further herein. In accordance with some embodiments of the present invention, the substituents of a substituted group are more particularly recited.

As used herein, the term "halo" and related terms, such as "halo group," "halo substituent," "halogen group," and "halogen substituent" means a single bonded halogen group, such as —F, —Cl, —Br, and —I.

As used herein, recitations of "halo substituted" and related terms (such as, but not limited to, haloalkyl groups, haloalkenyl groups, haloalkynyl groups, haloaryl groups, and halo-heteroaryl groups) means a group in which at least one, and up to and including all of the available hydrogen groups thereof is substituted with a halo group, such as, but not limited to, F, Cl or Br. The term "halo-substituted" is inclusive of "perhalo-substituted." As used herein, the term perhalo-substituted group and related terms (such as, but not limited to, perhaloalkyl groups, perhaloalkenyl groups, perhaloalkynyl groups, perhaloaryl groups or perhalo-heteroaryl groups) means a group in which all of the available hydrogen groups thereof are substituted with a halo group. For purposes of non-limiting illustration: perhalomethyl is —$CX_3$; and perhalophenyl is —$C_6X_5$, where X represents one or more halo groups, such as, but not limited to, F, Cl, Br, or I.

As used herein, "at least one of" is synonymous with "one or more of", whether the elements are listed conjunctively or disjunctively. For example, the phrases "at least one of A, B, and C" and "at least one of A, B, or C" each mean any one of A, B, or C, or any combination of any two or more of A, B, or C. For example, A alone; or B alone; or C alone; or A and B; or A and C; or B and C; or all of A, B, and C.

As used herein, "selected from" is synonymous with "chosen from" whether the elements are listed conjunctively or disjunctively. Further, the phrases "selected from A, B, and C" and "selected from A, B, or C" each mean any one of A, B, or C, or any combination of any two or more of A, B, or C. For example, A alone; or B alone; or C alone; or A and B; or A and C; or B and C; or all of A, B, and C.

The discussion of the present invention herein may describe certain features as being "particularly" or "preferably" within certain limitations (e.g., "preferably", "more preferably", or "even more preferably", within certain limitations). It is to be understood that the invention is not limited to or by such particular or preferred limitations, but, encompasses the entire scope of the disclosure.

As used herein, and in accordance with some embodiments, the term "ketone" such as with regard to groups, and substituents of various groups, of the compounds and components of the present invention, and related terms, such as "ketone group" and "ketone substituent", includes a material represented by —C(O)R, where R is selected from those groups as described below, other than hydrogen.

As used herein, and in accordance with some embodiments, the term "carboxylic acid" such as, with regard to groups, and substituents of various groups, of the compounds and components of the present invention, and related terms, such as, "carboxylic acid group" and "carboxylic acid substituent" includes a material represented by —C(O)OH.

As used herein, and in accordance with some embodiments, the term "ester" such as, with regard to groups, and substituents of various groups, of the compounds and components of the present invention, and related terms, such as "ester group" and "ester substituent" means a carboxylic acid ester group represented by —C(O)OR, where R is selected from those groups as described below, other than hydrogen.

As used herein, and in accordance with some embodiments, the term "carboxylate" such as, with regard to groups, and substituents of various groups, of the compounds and components of the present invention, and related terms, such as, "carboxylate group" and "carboxylate substituent," includes a material represented by —OC(O)R, where R is selected from those groups as described below.

As used herein, and in accordance with some embodiments, the term "amide" such as with regard to groups, and substituents of various groups, of the compounds and components of the present invention, and related terms, such as, "amide group" and "amide substituent" includes a material represented by —C(O)N(R)(R) or —N(R)C(O)R, where each R is independently selected from those groups as described below.

As used herein, and in accordance with some embodiments, the term "carbonate" such as with regard to groups, and substituents of various groups, of the compounds and components of the present invention, and related terms, such as, "carbonate group" and "carbonate substituent" includes a material represented by —OC(O)OR, where R is selected from those groups as described below, other than hydrogen.

As used herein, and in accordance with some embodiments, the term "carbamate" such as with regard to groups, and substituents of various groups, of the compounds and components of the present invention, and related terms, such as, "carbamate group" and "carbamate substituent" includes a material represented by —OC(O)N(R)(H) or —N(H)C(O)OR, where R in each case is independently selected from those groups as described below, other than hydrogen.

As used herein, and in accordance with some embodiments, the term "urea" such as with regard to groups, and substituents of various groups, of the compounds and components of the present invention, and related terms, such as, "urea group" and "urea substituent" includes a material represented by —N(R)C(O)N(R)(R), where each R is independently selected from those groups as described below.

As used herein, and in accordance with some embodiments, the term "siloxy" such as with regard to groups, and substituents of various groups, of the compounds and components of the present invention, and related terms, such as, "siloxy group" and "siloxy substituent" includes a material represented by —O—Si(R)$_3$ where each R is independently selected from those groups as described below, other than hydrogen.

As used herein, and in accordance with some embodiments, the term "alkoxysilane" such as, with regard to groups, and substituents of various groups, of the compounds and components of the present invention, and related terms, such as, "alkoxysilane group" and alkoxysilane substituent" includes a material represented by —Si(OR")$_w$(R)$_t$, where w is 1 to 3 and t is 0 to 2, provided the sum of w and t is 3; R" for each w is independently selected from alkyl; and R for each t is independently selected from those groups as described below, other than hydrogen.

As used herein, and in accordance with some embodiments, the term "polysiloxane" such as, with regard to groups, and substituents of various groups, of the compounds and components of the present invention, and related terms, such as, "polysiloxane group" and "polysiloxane substituent", includes a material represented by the following Formula (A):

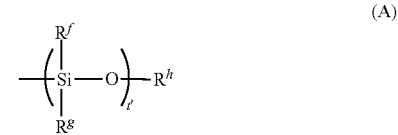

(A)

With reference to Formula (A): t' is greater than or equal to 2, such as, from 2 to 200; $R^f$ and $R^g$ for each t' are each independently selected from a group R as described below, other than hydrogen; and $R^h$ is independently a group R as described below.

Unless otherwise stated, each R group of each of the above described ketone, ester (carboxylic acid ester), carboxylate, amide, carbonate, carbamate, urea, siloxane, alkoxysilane groups, and polysiloxane groups, is in each case independently selected from hydrogen, alkyl, haloalkyl, perhaloalkyl, cycloalkyl, heterocycloalkyl, aryl, heteroaryl, and combinations thereof (including those classes and examples thereof as recited previously herein).

The anodically-coloring electrochromic compounds of the present invention, such as, but not limited to, those represented by Formula (I), and the various groups thereof, are described in further detail herein as follows.

With some embodiments of the present invention and with reference to Formula (I), $R^1$ and $R^2$ are each independently selected from linear or branched $C_3$-$C_{20}$ alkyl.

With some further embodiments of the present invention and with reference to Formula (I), $R^1$ and $R^2$ are each independently selected from linear or branched $C_3$-$C_{10}$ alkyl.

With some additional embodiments of the present invention and with reference to Formula (I), $R^1$ and $R^2$ are each independently selected from linear or branched $C_4$-$C_8$ alkyl.

In accordance with some embodiments, examples of alkyl groups from which $R^1$ and $R^2$ of Formula (I) can be each independently selected, include, but are not limited to, n-propyl, iso-propyl, n-butyl, sec-butyl, tert-butyl, n-pentyl, branched-pentyl, n-hexyl, branched-hexyl, n-heptyl, branched-heptyl, n-octyl, branched-octyl, n-nonyl, branched-nonyl, n-decyl, branched-decyl, n-undecyl, branched-undecyl, n-dodecyl, branched-dodecyl, n-tridecyl, branched-tridecyl, n-tetradecyl, branched-tetradecyl, n-pentadecyl, branched-pentadecyl, n-hexadecyl, branched-hexadecyl, n-heptadecyl, branched-heptadecyl, n-octadecyl, branched-octadecyl, n-nonadecyl, branched-nonadecyl, n-icosanyl, and branched-icosanyl.

The anodically-coloring electrochromic compounds of the present invention, such as, represented by Formula (I), can be prepared in accordance with art-recognized methods. With some embodiments, the anodically-coloring electrochromic compounds of the present invention, such as represented by Formula (I), can be prepared in accordance with the following general and non-limiting description. With reference to Scheme-(1) below, compound (1) (2,3-dihydrothieno[3,4-b][1,4]dioxine) is treated with n-butyl lithium (nBuLi) in tetrahydrofuran (THF) at −78° C., followed by quenching with a disulfide (R—SS—R), and subsequent purification/isolation using chromatography, which results in the formation of compound (2) (5-(R-thio)-2,3-dihydrothieno[3,4-b][1,4]dioxine). Compound (2) is treated with n-butyl lithium (nBuLi) in tetrahydrofuran (THF) at −78° C., followed by combination with iron(III) tris(acetylacetonate) (Fe(AcAc)$_3$), which results in the formation of compound (3). In Scheme-(1), the R groups of the disulfide and compound (3) are each independently selected from linear or branched $C_3$-$C_{20}$ alkyl.

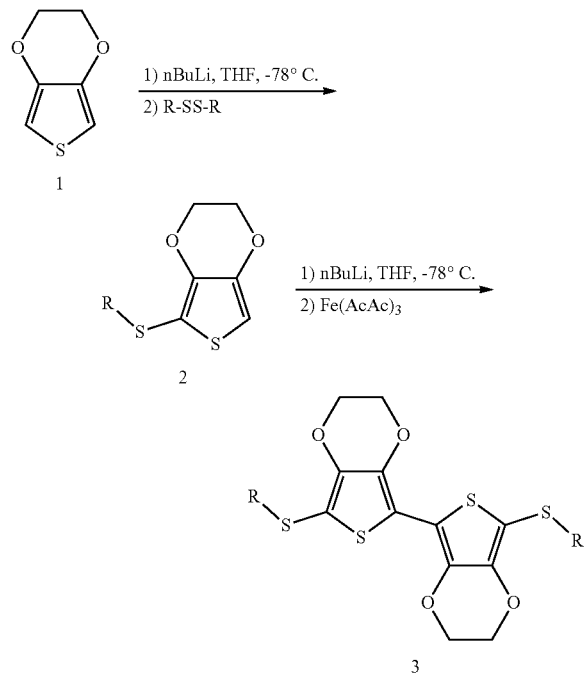

Scheme-(1)

In accordance with some embodiments of the present invention there is provided an electrochromic device. For purposes of non-limiting illustration, an electrochromic device (3) according to the present invention is depicted in FIG. 1. Electrochromic device (3) includes a first substrate (11) having a first surface (14) and a second surface (17). First surface (14) of first substrate (11) includes a first transparent electrode layer (20), which is electrically conductive. First transparent electrode layer (20) resides over at least a portion of first surface (14) of first substrate (11). With some embodiments, first transparent electrode layer (20) is in the form of one or more patterns (such as, one or more designs and/or indicia) over first surface (14) of first substrate (11). With some further embodiments, first transparent electrode layer (20) forms a substantially continuous layer over first surface (14) of first substrate (11). First transparent electrode layer (20) is, with some embodiments, in electrical contact with at least one first electrical conductor (21), which can be a first electrically conductive wire.

Electrochromic device (3) includes a second substrate (23) having a first surface (26) and a second surface (29). First surface (26) of second substrate (23) includes a second transparent electrode layer (32), which is electrically conductive. Second transparent electrode layer (32) resides over at least a portion of first surface (26) of second substrate (23). With some embodiments, second transparent electrode layer (32) is in the form of one or more patterns (such as, one or more designs and/or indicia) over first surface (26) of second substrate (23). With some further embodiments, second transparent electrode layer (32) forms a substantially continuous layer over first surface (26) of second substrate (23). Second transparent electrode layer (32) is, with some embodiments, in electrical contact with at least one second electrical conductor (33), which can be a second electrically conductive second wire.

With further reference to electrochromic device (3) of FIG. 1, first transparent electrode layer (20) and second transparent electrode layer (32) are in opposing spaced facing opposition relative to each other.

Electrochromic device (3) further includes an electrochromic layer (35) that is interposed between first transparent electrode layer (20) and second transparent electrode layer (32). With some embodiments, electrochromic layer (35) is interposed between and in abutting relationship with first transparent electrode layer (20) and second transparent electrode layer (32).

Figure 2:
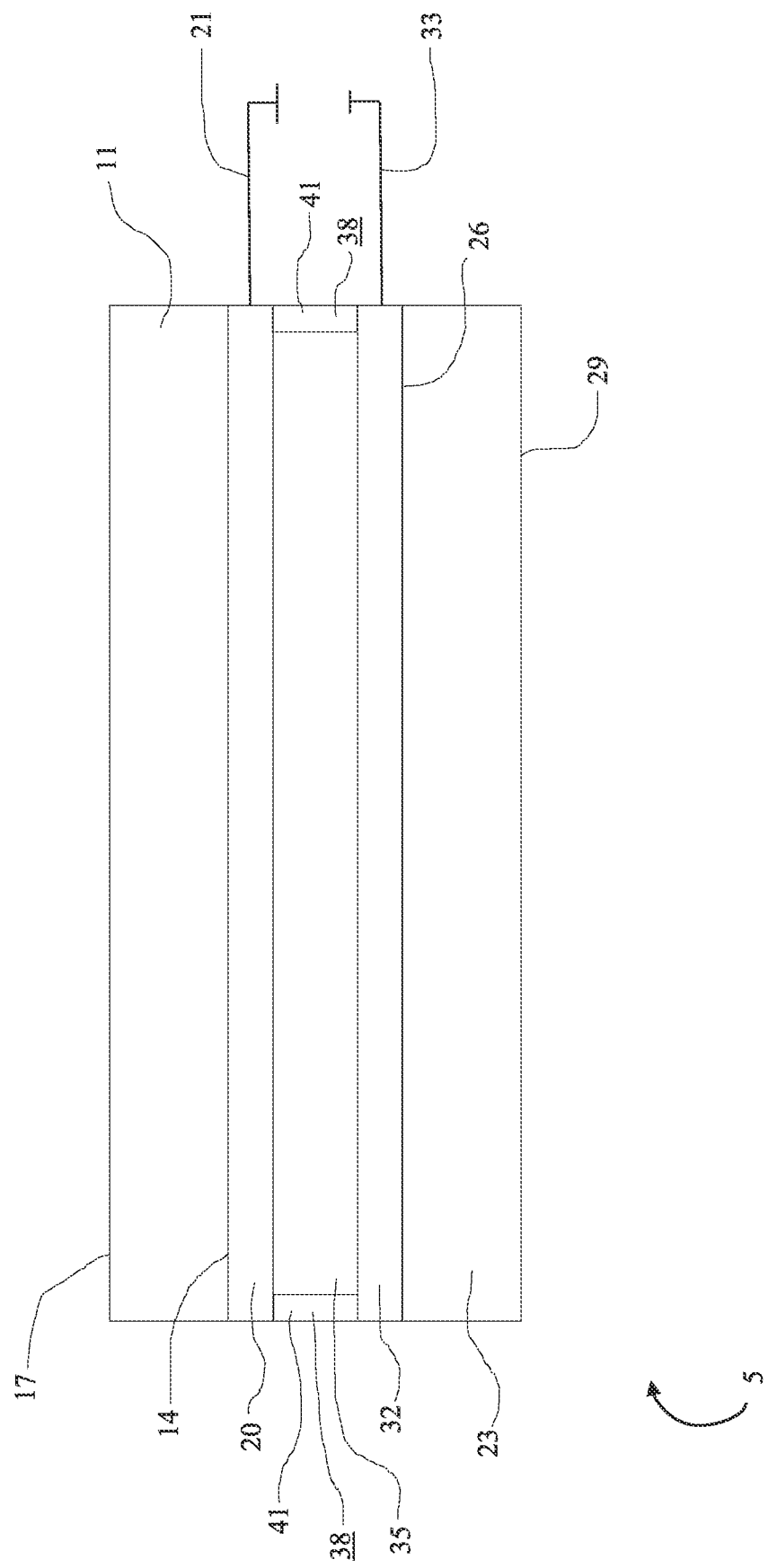
FIG. 2 is a representative side elevational sectional view of an electrochromic device according to the present invention, which further includes a gasket that serves to seal the electrochromic layer.

In accordance with some embodiments of the present invention, the electrochromic device further includes a gasket that serves to at least seal the electrochromic layer. With non-limiting reference to FIG. 2, electrochromic device (5), which is similar to electrochromic device (3), further includes a gasket (41) that resides in a recess (38) that extends around the whole of electrochromic device (5). With some embodiments recess (38) is an annular ring (38). With further reference to FIG. 2, first substrate (11) and first transparent electrode layer (20), and second substrate (23) and second transparent electrode layer (32) extend laterally outward over/relative to electrochromic layer (35). The portions of first transparent electrode layer (20) and second transparent electrode layer (32), that extend laterally outward relative to electrochromic layer (35), together define recess (38) in which gasket (41) resides. With some embodiments, gasket (41) has oxygen-barrier properties and serves to minimize contact of oxygen with electrochromic layer (35) after electrochromic device (5) is fabricated. Gasket (41), with some embodiments, is composed of organic polymers and/or ceramic materials. In accordance with some embodiments, gasket (41) is placed and positioned within recess (38) prior to vacuum lamination of the stack, as described further herein.

The first substrate and the second substrate of the electrochromic devices are, with some embodiments of the present invention, each independently selected from transparent substrates. Transparent substrates, from which the first and second substrates can each be independently selected, are with some embodiments, fabricated from materials including, but not limited to, silica glass, organic polymers (such as, but not limited to, polycarbonate polymers), and combinations thereof. With some embodiments, the transparent substrates, from which the first and second substrates can each be independently selected, are fabricated from materials including silica glass. The first and second substrates can each independently have any suitable thickness. With some embodiments, the first and second substrates each independently have a thickness of from 2 mm to 10 mm.

The first and second transparent electrode layers of the electrochromic devices of the present invention, with some embodiments, include electrically conductive inorganic oxides, electrically conductive organic materials, electrically conductive metals, and/or electrically conductive carbon, such as, carbon nanotubes and/or graphene. Examples of electrically conductive inorganic oxides, include, but are not limited to: tin oxide, which can be doped with a doping material, such as, indium; and zinc oxide, which can further include, for example, aluminum. Examples of electrically conductive organic materials include, but are not limited to, poly(3,4-ethylenedioxythiophene), poly(4,4-dioctyl cyclopentadithiophene), and poly(3,4-ethylenedioxythiophene):poly(styrene sulfonate). The first and second transparent electrode layers, with some embodiments, can each independently be in the form of a grid of metal wires, a grid of carbon nanotubes, and/or a layer of graphene. With some embodiments, the first and second transparent electrode layers are each independently selected from semi-transparent metal layers. With some further embodiments, one of the first and second transparent electrode layers includes (or has associated therewith) a reflective metal layer (including, for example, aluminum, gold, and/or silver) and the electrochromic device is a reflective electrochromic device, such as, a controllably reflective mirror.

In accordance with some embodiments, the first and second electrode layers of the electrochromic devices of the present invention, each independently include an electrically conductive material selected from indium-tin-oxide, poly(3,4-ethylenedioxythiophene):poly(styrene sulfonate), or combinations thereof.

The first and second electrode layers of the electrochromic devices, in accordance with some embodiments of the present invention, can each independently have any suitable thickness, provided they are both transparent and electrically conductive. With some embodiments, the first and second electrode layers of the electrochromic devices of the present invention, each independently have a thickness of from 0.01 micrometers to 10 micrometers.

The electrochromic layer of the electrochromic devices of the present invention includes an anodic component, which includes an anodically-coloring electrochromic compound represented by Formula (I), as described previously herein.

In addition to the anodically-coloring electrochromic compound represented by Formula (I), the anodic component of the electrochromic layer, with some embodiments, optionally, includes one or more additional anodic electrochromic compounds, such as, but not limited to: ferrocene and/or ferrocene derivatives (in which at least one cyclopentadienyl ring thereof is substituted with at least one substituent, including those substituents recited previously herein); 5,10-dihydro-5,10-di(linear or branched $C_1$-$C_{10}$ alkyl)phenazine, such as 5,10-dihydro-5,10-dimethylphenazine; N-substituted phenoxazine, such as, N-phenylphenoxazine; and combinations thereof.

With some embodiments, the anodic component of the electrochromic layer of the electrochromic devices of the present invention consists essentially of an anodically-coloring electrochromic compound represented by Formula (I), as described previously herein. With some further embodiments, the anodic component of the electrochromic layer of the electrochromic devices of the present invention consists of an anodically-coloring electrochromic compound represented by Formula (I), as described previously herein.

The electrochromic layer of the electrochromic devices of the present invention includes a cathodic component. The cathodic component includes, with some embodiments, at least one material that is reversibly reduced, as the anodically-coloring electrochromic material represented by Formula (I) is reversibly oxidized. With some embodiments, the cathodic component includes one or more dipyridinium (or dipyridinium based) cations (such as, including or based on, but not limited to, 4,4'-dipyridinium, 2,2'-dipyridinium, 1,1'-dipyidinium, and/or a 1,1'-dipyridinium in which the nitrogen atoms are linked by a divalent linking group, such as, a divalent alkyl linking group) and/or derivatives thereof, in which, optionally, one or more of the quaternary nitrogen atoms are bonded to a group other than hydrogen, such as, an alkyl group or an aryl group.

With some embodiments, the cathodic component includes a 1,1'-disubstituted-4,4'-dipyridinium cation represented by the following Formula (II),

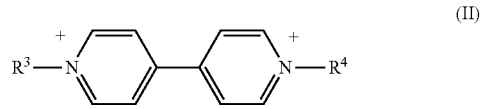

(II)

With reference to Formula (II), $R^3$ and $R^4$ are each independently selected from linear or branched $C_1$-$C_{10}$ alkyl, unsubstituted aryl, and substituted aryl. The aryl groups of the unsubstituted aryl groups and substituted aryl groups, from which $R^3$ and $R^4$ can each be independently selected, include those aryl groups as recited previously herein, such as, but not limited to, phenyl, naphthyl, phenanthryl, and anthracenyl. The substituents of the substituted aryl groups, from which $R^3$ and $R^4$ can each be independently selected, include those substituents as recited previously herein. With some embodiments, each substituent of the substituted aryl groups, from which $R^3$ and $R^4$ can each be independently selected, are each independently selected from: alkoxy groups; halo groups (e.g., F, Cl, I, and Br); hydroxyl groups; thiol groups; alkylthio groups; arylthio groups; ketone groups; aldehyde groups; haloalkyl groups; perhaloalkyl groups; heterocycloalkyl groups; aryl groups; aralkyl groups (such as, benzyl groups); heteroaryl groups; and amino groups.

With further reference to Figure (II), and in accordance with some further embodiments, $R^3$ and $R^4$ are each independently selected from linear or branched $C_1$-$C_4$ alkyl, unsubstituted phenyl, and substituted phenyl. Each substituent of the substituted phenyl groups, from which $R^3$ and $R^4$ can each be independently selected, include those substituents as recited previously herein. With some embodiments, each substituent of the substituted phenyl groups, from which $R^3$ and $R^4$ can each be independently selected, are each independently selected from: alkoxy groups; halo groups (e.g., F, Cl, I, and Br); hydroxyl groups; thiol groups; alkylthio groups; arylthio groups; ketone groups; aldehyde groups; haloalkyl groups; perhaloalkyl groups; aryl groups; and aralkyl groups (such as, benzyl groups).

In accordance with some embodiments, and with additional reference to Formula (II), $R^3$ is selected from linear or branched $C_1$-$C_{10}$ alkyl, and $R^4$ is selected from aryl and substituted aryl. With some additional embodiments, $R^3$ is selected from linear or branched $C_1$-$C_4$ alkyl, and $R^4$ is selected from unsubstituted phenyl, and substituted phenyl.

With some embodiments, the cathode component includes, in addition to or alternatively to the 1,1'-disubstituted-4,4'-dipyridinium cation represented by Formula (II), a 1,1-(alkane-alpha, omega-diyl)-bis-(1'-substituted-4,4'-dipyridinium) cation represented by the following Formula (III):

(III)

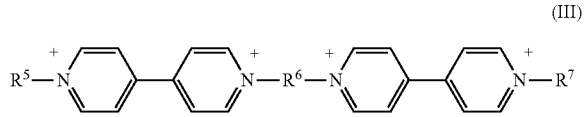

With reference to Formula (III), and in accordance with some embodiments, $R^5$ and $R^7$ are each independently selected from linear or branched $C_1$-$C_{10}$ alkyl, unsubstituted aryl, and substituted aryl. The aryl groups of the unsubstituted aryl groups and substituted aryl groups, from which $R^5$ and $R^7$ can each be independently selected, include those aryl groups as recited previously herein, such as, but not limited to, phenyl, naphthyl, phenanthryl, and anthracenyl. The substituents of the substituted aryl groups, from which $R^5$ and $R^7$ can each be independently selected, include those substituents as recited previously herein. With some embodiments, each substituent of the substituted aryl groups, from which $R^5$ and $R^7$ can each be independently selected, are each independently selected from: alkoxy groups; halo groups (e.g., F, Cl, I, and Br); hydroxyl groups; thiol groups; alkylthio groups; arylthio groups; ketone groups; aldehyde groups; haloalkyl groups; perhaloalkyl groups; heterocycloalkyl groups; aryl groups; aralkyl groups (such as, benzyl groups); heteroaryl groups; and amino groups.

With further reference to Formula (III), and in accordance with some further embodiments, $R^5$ and $R^7$ are each independently selected from linear or branched $C_1$-$C_4$ alkyl, unsubstituted phenyl, and substituted phenyl. Each substituent of the substituted phenyl groups, from which $R^5$ and $R^7$ can each be independently selected, include those substituents as recited previously herein. With some embodiments, each substituent of the substituted phenyl groups, from which $R^5$ and $R^7$ can each be independently selected, are each independently selected from: alkoxy groups; halo groups (e.g., F, Cl, I, and Br); hydroxyl groups; thiol groups; alkylthio groups; arylthio groups; ketone groups; aldehyde groups; haloalkyl groups; perhaloalkyl groups; aryl groups; and aralkyl groups (such as, benzyl groups).

With further reference to Formula (III), $R^6$ is a divalent linear or branched $C_1$-$C_{10}$ alkane linking group. With some embodiments, $R^6$ of Formula (II) is a divalent linear or branched $C_1$-$C_8$ alkane linking group. With some further embodiments, $R^6$ of Formula (III) is a divalent linear or branched $C_3$-$C_5$ alkane linking group.

In accordance with some embodiments of the present invention, the cathodic component further includes counter-anions. With some further embodiments, the cathodic component includes an equal number of cations and counter-anions (or anions), and, correspondingly, the cathodic component has a net neutral charge. Each counter-anion of the cathodic component, with some embodiments, is independently selected from the group consisting of $BF_4^-$, $PF_6^-$, $ClO_4^-$, $CF_3SO_3^-$ or $(CF_3SO_2)_2N^-$ and $(CF_3SO_2)_3C^-$.

The electrochromic layer of the electrochromic device of the present invention further includes an electrolyte. The electrolyte includes, with some embodiments, at least one electrolyte anion and at least one electrolyte cation. The electrolyte of the electrochromic layer includes, with some embodiments, an equal number of electrolyte anions and electrolyte cations, and, correspondingly, has a net neutral charge.

With some embodiments, the electrolyte of the electrochromic layer includes at least one electrolyte anion, where each electrolyte anion is independently selected from chloride, hexafluorophosphate, and bis(perfluoro(linear or branched $C_1$-$C_6$ alkysulfonyl)imide. With some further embodiments, the electrolyte of the electrochromic layer includes at least one electrolyte cation, where each electrolyte cation is independently selected from sodium, potassium, lithium, 1-(linear or branched $C_1$-$C_6$ alkyl)-3-(linear or branched $C_1$-$C_6$ alkyl)imidazolium, and 1-(linear or branched $C_1$-$C_6$ alkyl)-1-(linear or branched $C_1$-$C_6$ alkyl)piperidinium.

The electrolyte of the electrochromic layer, with some embodiments includes: at least one electrolyte anion, where each electrolyte anion is independently selected from bis (perfluoro(linear or branched $C_1$-$C_6$ alkysulfonyl)imide; and at least one electrolyte cation, wherein each electrolyte cation is independently selected from 1-(linear or branched $C_1$-$C_6$ alkyl)-3-(linear or branched $C_1$-$C_6$ alkyl)imidazolium, or 1-(linear or branched $C_1$-$C_6$ alkyl)-1-(linear or branched $C_1$-$C_6$ alkyl)piperidinium.

The electrolyte of the electrochromic layer, with some further embodiments includes: at least one electrolyte anion, where each electrolyte anion is bis(trifluromethylsulfonyl) imide; and at least one electrolyte cation, where each electrolyte cation is independently selected from 1-ethyl-3-methylimidazolium, 1-butyl-3-methylimidazolium, and 1-methyl-1-propylpiperidinium.

The electrochromic layer, of the electrochromic devices of the present invention, includes a polymer matrix. The polymer matrix includes at least one polymer. The polymer matrix, with some embodiments, is a gelled polymer matrix, a crosslinked polymer matrix, and/or a thermoplastic polymer matrix.

With some embodiments, the polymer matrix includes a polymer, where the polymer includes at least one of poly ((meth)acrylonitrile), poly(vinylidene fluoride), poly(vinylidene fluoride-co-perfluoro(linear or branched $C_1$-$C_6$ alkylene)), or poly((linear or branched $C_1$-$C_8$ alkyl)(meth) acrylate).

In accordance with some embodiments of the electrochromic device of the present invention: the cathodic component is present in an amount of from 0.8 percent by weight to 6.25 percent by weight; the anodic component is present in an amount of from 0.8 percent by weight to 6.25 percent by weight; the electrolyte is present in an amount of from 16.4 percent by weight to 25.0 percent by weight; and the polymer matrix is present in an amount of from 62.5 percent by weight to 82.0 percent by weight. The percent weights in each case are based on total weight of the cathodic component, the anodic component, the electrolyte, and the polymer matrix.

The electrochromic layer of the electrochromic devices of the present invention can, with some embodiments, further include one or more art-recognized optional additives, such as, but not limited to, thermal stabilizers, UV stabilizers, rheology modifiers, static coloring agents (such as, static tints and/or static dyes), kinetic additives (that accelerate electrode reaction) and combinations thereof. A non-limiting class of art-recognized thermal stabilizers are phenols, such as 2,6-ditertiarybutylphenol and compounds including 2,6-ditertiarybutylphenol groups or moieties. A non-limiting class of art-recognized UV stabilizers are hindered amine light stabilizers (HALS), such as, 2,2,6,6-tetramethylpiperidine and compounds including 2,2,6,6-tetramehtylpiperidine groups or moieties. Static coloring agents include coloring agents for which the absorption spectrum thereof does not change in response to actinic radiation (such as, UV and/or visible light) or the application of an electric potential, and do not include photochromic compounds and electrochromic compounds. A non-limiting class of kinetic additives includes salts, such as: alkali and alkaline earth metal salts of perchlorates, tetrafluoroborates, and hexafluorophosphates; and tetralkylammonium salts. Non-limiting examples of rheology modifies include: dialkoxyacetophenones, such as 3',4'dimethoxyacetophenone; and optionally substituted cycloalkylarylketones, such as, 1-hydroxycyclohexyl phenyl ketone. Each optional additive can be present in any suitable active amount, such as from 0.05 percent by weight to 5 percent by weight, based on the total solids weight of the electrochromic layer (including the weight of the optional additive(s)).

Examples of articles, such as, articles of manufacture, that may include or be defined by the electrochromic devices of the present invention include, but, are not limited to: energy efficient and/or privacy transparencies (or windows), such as, architectural and transportation transparencies or windows; mirrors, such as, rearview mirrors; optical filters; and ophthalmic articles, such as, corrective lenses, non-corrective lenses, magnifying lenses, protective lenses, and visors; and any other article or application where variable and controllable light transmission and/or color is desired.

The present invention also relates to an electrochromic composition that includes: (i) a cathodic component; (ii) an anodic component; (iii) an electrolyte; a polymeric thickener; and (v) a solvent. The anodic component of the electrochromic compositions of the present invention includes an anodically-coloring electrochromic compound represented by Formula (I) as described previously herein.

The cathodic component, anodic component, and electrolyte of the electrochromic composition are each as described previously herein with regard to the electrochromic layer of the electrochromic device of the present invention.

The polymeric thickener of the electrochromic composition of the electrochromic composition includes, with some embodiments, a polymer, where the polymer includes at least one of poly((meth)acrylonitrile), poly(vinylidene fluoride), poly(vinylidene fluoride-co-perfluoro(linear or branched $C_1$-$C_6$ alkylene)), or poly((linear or branched $C_1$-$C_8$ alkyl)(meth)acrylate).

The electrochromic composition of the present invention includes a solvent. With some embodiments, the solvent of the electrochromic composition includes at least one of ethylene carbonate, propylene carbonate, gamma-butyrolactone, gamma-valerolactone, N-methylpyrrolidone, polyethylene glycol, or carboxylic acid esters of polyethylene glycol.

In accordance with some embodiments of the electrochromic composition of the present invention: the cathodic component is present in an amount of from 0.2 percent by weight to 3.6 percent by weight; the anodic component is present in an amount of from 0.2 percent by weight to 3.6 percent by weight; the electrolyte is present in an amount of from 3.8 percent by weight to 14.3 percent by weight; the polymeric thickener is present in an amount of from 19.2 percent by weight to 35.7 percent by weight; and the solvent is present in an amount of from 42.8 percent by weight to 76.6 percent by weight. The percent weights in each case are based on total weight of the cathodic component, the anodic component, the electrolyte, the polymeric thickener, and the solvent.

The electrochromic composition of the present invention can, with some embodiments, include one or more art-recognized optional additives, such as, but not limited to, thermal stabilizers, UV stabilizers, rheology modifiers, static coloring agents (such as static tints and/or static dyes), kinetic additives (that accelerate electrode reaction) and combinations thereof. The optional additives are in each case as described previously herein with regard to the electrochromic device of the present invention. Each optional additive can be present in the electrochromic composition in any suitable active amount, such as, from 0.05 percent by weight to 5 percent by weight, based on the total weight of the electrochromic composition (including the weight of the optional additive(s)).

In accordance with some embodiments of the present invention, the electrochromic layer of the electrochromic device is formed from the electrochromic composition of the present invention. In accordance with some embodiments of the present invention, formation of the electrochromic composition and electrochromic layer includes the following steps. First, all components of the electrochromic composition, other than the polymeric thickener, are mixed under sheer (such as with an impeller) until a homogenous mixture is formed. Secondly, the polymeric thickener is added, and the combination is subjected to homogenization, which results in the formation of a thick slurry. A liquid film of the thick slurry is formed, such as, using a doctor blade or draw-down bar, on a sacrificial or temporary liner (composed of polyethylene terephthalate, in some embodiments). The liquid film while on the sacrificial/temporary liner is subjected to elevated temperature, such as from 60° to 90° C. for 3 to 10 minutes, which results in the formation of a solidified film/layer, which is the electrochromic layer. The solidified film/electrochromic layer, is separated from the sacrificial/temporary liner (which is discarded), cut to size (if necessary), and placed over or onto a first transparent electrode layer of a first substrate. The second transparent electrode of a second substrate is positioned over or onto the other (or facing/exposed) side of the electrochromic layer, to form a stack that includes the first substrate, the first transparent electrode, the electrochromic layer, the second transparent electrode, and the second substrate. The stack may further include electrical connectors that are in separate electrical contact with the first and second transparent electrodes. The stack (with an optional gasket surrounding the outer edges of at least the electrochromic layer) is subjected to vacuum lamination, with the concurrent application of elevated temperature, such as from 110° C. to 200° C., for a period of time, such as from 10 to 30 minutes. After cooling, the so formed electrochromic device is removed from vacuum lamination device.

The present invention can further be characterized by one or more of the following non-limiting clauses.

Clause 1: An electrochromic device comprising:
(a) a first substrate having a surface comprising a first transparent electrode layer;
(b) a second substrate having a surface comprising a second transparent conductive electrode layer,
wherein said first transparent electrode layer and said second transparent electrode layer are in opposing spaced opposition; and
(c) an electrochromic layer interposed between said first transparent electrically conductive electrode layer and said second transparent electrically conductive electrode layer, wherein said electrochromic layer comprises,
(i) a cathodic component,
(ii) an anodic component,
(iii) an electrolyte, and
(iv) a polymer matrix,
wherein said anodic component comprises an anodically-coloring electrochromic compound represented by the following Formula (I),

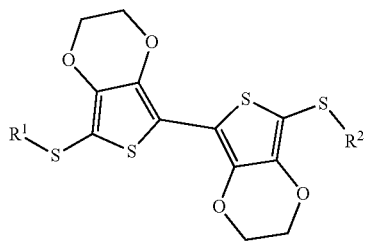

wherein $R^1$ and $R^2$ are each independently selected from linear or branched $C_3$-$C_{20}$ alkyl.

Clause 2: The electrochromic device of clause 1, wherein $R^1$ and $R^2$ are each independently linear or branched $C_3$-$C_{10}$ alkyl.

Clause 3: The electrochromic device of clauses 1 or 2, wherein $R^1$ and $R^2$ are each independently linear or branched $C_4$-$C_8$ alkyl.

Clause 4: The electrochromic device of any one of clauses 1, 2, or 3, wherein said cathodic component comprises a 1,1'-disubstituted-4,4'-dipyridinium cation represented by the following Formula (II),

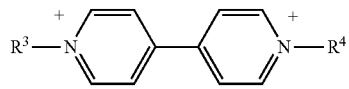

wherein $R^3$ and $R^4$ are each independently selected from linear or branched $C_1$-$C_{10}$ alkyl, unsubstituted aryl, and substituted aryl.

Clause 5: The electrochromic device of clause 4, wherein $R^3$ and $R^4$ are each independently selected from linear or branched $C_1$-$C_4$ alkyl, unsubstituted phenyl, and substituted phenyl.

Clause 6: The electrochromic device of clauses 4 or 5, wherein $R^3$ is selected from linear or branched $C_1$-$C_4$ alkyl, and $R^4$ is selected from unsubstituted phenyl, and substituted phenyl.

Clause 7: The electrochromic device of any one of clauses 1, 2, 3, 4, 5, or 6, wherein said cathodic component further comprises counter-anions, wherein each counter-anion of the cathodic component is independently selected from the group consisting of $BF_4^-$, $PF_6^-$, $ClO_4^-$, $CF_3SO_3^-$ or $(CF_3SO_2)_2N^-$ and $(CF_3SO_2)_3C^-$.

Clause 8: The electrochromic device of any one of clauses 1, 2, 3, 4, 5, 6, or 7, wherein said electrolyte comprises,
at least one electrolyte anion, wherein each electrolyte anion is independently selected from bis(perfluoro(linear or branched $C_1$-$C_6$ alkysulfonyl)imide, and
at least one electrolyte cation, wherein each electrolyte cation is independently selected from 1-(linear or branched $C_1$-$C_6$ alkyl)-3-(linear or branched $C_1$-$C_6$ alkyl) imidazolium, or 1-(linear or branched $C_1$-$C_6$ alkyl)-1-(linear or branched $C_1$-$C_6$ alkyl)piperidinium.

Clause 9: The electrochromic device of any one of clauses 1, 2, 3, 4, 5, 6, 7, or 8, wherein said polymer matrix comprises a polymer, wherein said polymer comprises at least one of poly((meth)acrylonitrile), poly(vinylidene fluoride), poly(vinylidene fluoride-co-perfluoro(linear or branched $C_1$-$C_6$ alkylene)), or poly((linear or branched $C_1$-$C_8$ alkyl)(meth)acrylate).

Clause 10: The electrochromic device of any one of clauses 1, 2, 3, 4, 5, 6, 7, 8, or 9 wherein,
said cathodic component is present in an amount of from 0.8 percent by weight to 6.25 percent by weight,
said anodic component is present in an amount of from 0.8 percent by weight to 6.25 percent by weight,
said electrolyte is present in an amount of from 16.4 percent by weight to 25.0 percent by weight, and
said polymer matrix is present in an amount of from 62.5 percent by weight to 82.0 percent by weight,
the percent weights in each case being based on total weight of said cathodic component, said anodic component, said electrolyte, and said polymer matrix.

Clause 11: An electrochromic composition comprising,
(i) a cathodic component,
(ii) an anodic component,
(iii) an electrolyte,
(iv) a polymeric thickener, and
(v) a solvent,
wherein said anodic component comprises an anodically-coloring electrochromic compound represented by the following Formula (I),

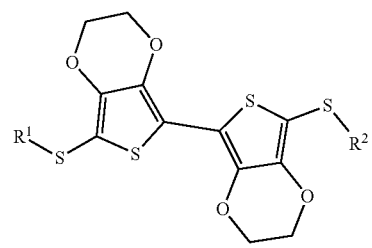

wherein $R^1$ and $R^2$ are each independently selected from linear or branched $C_3$-$C_{20}$ alkyl.

Clause 12: The electrochromic composition of clause 11, wherein $R^1$ and $R^2$ are each independently $C_3$-$C_{10}$ alkyl.

Clause 13: The electrochromic composition of clauses 11 or 12, wherein $R^1$ and $R^2$ are each independently linear or branched $C_4$-$C_8$ alkyl.

Clause 14: The electrochromic composition of any one of clauses 11, 12, or 13, wherein said cathodic component comprises a 1,1'-disubstituted-4,4'-dipyridinium cation represented by the following Formula (II),

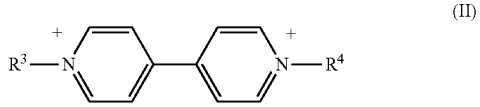

(II)

wherein $R^3$ and $R^4$ are each independently selected from linear or branched $C_1$-$C_{10}$ alkyl, unsubstituted aryl, and substituted aryl.

Clause 15: The electrochromic composition of clause 13, wherein $R^3$ and $R^4$ are each independently selected from linear or branched $C_1$-$C_4$ alkyl, unsubstituted phenyl, and substituted phenyl.

Clause. 16: The electrochromic composition of clauses 14 or 15, wherein $R^3$ is selected from linear or branched $C_1$-$C_4$ alkyl, and $R^4$ is selected from unsubstituted phenyl, and substituted phenyl.

Clause 17: The electrochromic composition of any one of clauses 11, 12, 13, 14, 15, or 16, wherein, said cathodic component further comprises counter-anions, wherein each counter-anion of the cathodic component is selected from the group consisting of $BF_4^-$, $PF_6^-$, $ClO_4^-$, $CF_3SO_3^-$ or $(CF_3SO_2)_2N^-$ and $(CF_3SO_2)_3C^-$.

Clause 18: The electrochromic composition of any one of clauses 11, 12, 13, 14, 15, 16, or 17, wherein said electrolyte comprises, at least one electrolyte anion, wherein each electrolyte anion is independently selected from bis(perfluoro(linear or branched $C_1$-$C_6$ alkylsulfonyl)imide, and at least one electrolyte cation, wherein each electrolyte cation is independently selected from 1-(linear or branched $C_1$-$C_6$ alkyl)-3-(linear or branched $C_1$-$C_6$ alkyl) imidazolium, or 1-(linear or branched $C_1$-$C_6$ alkyl)-1-(linear or branched $C_1$-$C_6$ alkyl)piperidinium.

Clause 19: The electrochromic composition of any one of clauses 11, 12, 13, 14, 15, 16, 17, or 18, wherein said polymeric thickener comprises a polymer, wherein said polymer comprises at least one of poly((meth)acrylonitrile), poly(vinylidene fluoride), poly(vinylidene fluoride-co-perfluoro(linear or branched $C_1$-$C_6$ alkylene)), or poly((linear or branched $C_1$-$C_8$ alkyl)(meth)acrylate).

Clause 20: The electrochromic composition of any one of clauses 11, 12, 13, 14, 15, 16, 17, 18, or 19, wherein said solvent comprises at least one of ethylene carbonate, propylene carbonate, gamma-butyrolactone, gamma-valerolactone, N-methylpyrrolidone, polyethylene glycol, or carboxylic acid esters of polyethylene glycol.

Clause 21: The electrochromic composition of any one of clauses 11, 12, 13, 14, 15, 16, 17, 18, 19, or 20, wherein, said cathodic component is present in an amount of from 0.2 percent by weight to 3.6 percent by weight,
said anodic component is present in an amount of from 0.2 percent by weight to 3.6 percent by weight,
said electrolyte is present in an amount of from 3.8 percent by weight to 14.3 percent by weight,
said polymeric thickener is present in an amount of from 19.2 percent by weight to 35.7 percent by weight, and
said solvent is present in an amount of from 42.8 percent by weight to 76.6 percent by weight,
the percent weights in each case being based on total weight of said cathodic component, said anodic component, said electrolyte, said polymeric thickener, and said solvent.

Clause 22: An anodically-coloring electrochromic compound represented by the following Formula (I),

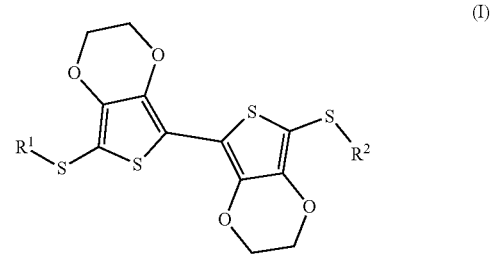

(I)

wherein $R^1$ and $R^2$ are each independently selected from linear or branched $C_3$-$C_{20}$ alkyl.

Clause 23: The anodically-coloring electrochromic compound of clause 21, wherein $R^1$ and $R^2$ are each independently linear or branched $C_3$-$C_{10}$ alkyl.

Clause 24: The anodically-coloring electrochromic compound of clauses 22 or 23, wherein $R^1$ and $R^2$ are each independently linear or branched $C_4$-$C_5$ alkyl.

The present invention has been described with reference to specific details of particular embodiments thereof. It is not intended that such details be regarded as limitations upon the scope of the invention except insofar as to the extent that they are included in the accompanying claims.

What is claimed is:

1. An electrochromic device comprising:
(a) a first substrate having a surface comprising a first transparent electrode layer;
(b) a second substrate having a surface comprising a second transparent conductive electrode layer,
wherein said first transparent electrode layer and said second transparent electrode layer are in opposing spaced opposition; and
(c) an electrochromic layer interposed between said first transparent electrically conductive electrode layer and said second transparent electrically conductive electrode layer, wherein said electrochromic layer comprises,
(i) a cathodic component,
(ii) an anodic component,
(iii) an electrolyte, and
(iv) a polymer matrix,
wherein said anodic component comprises an anodically-coloring electrochromic compound represented by the following Formula (I),

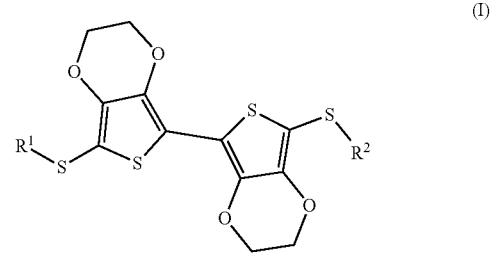

(I)

wherein R¹ and R² are each independently selected from linear or branched $C_3$-$C_{20}$ alkyl.

2. The electrochromic device of claim 1, wherein R¹ and R² are each independently linear or branched $C_3$-$C_{10}$ alkyl.

3. The electrochromic device of claim 2, wherein R¹ and R² are each independently linear or branched $C_4$-$C_8$ alkyl.

4. The electrochromic device of claim 1, wherein said cathodic component comprises a 1,1'-disubstituted-4,4'-dipyridinium cation represented by the following Formula (II),

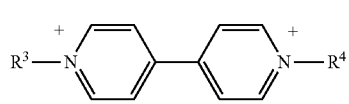
(II)

wherein R³ and R⁴ are each independently selected from linear or branched $C_1$-$C_{10}$ alkyl, unsubstituted aryl, and substituted aryl.

5. The electrochromic device of claim 4, wherein R³ and R⁴ are each independently selected from linear or branched $C_1$-$C_4$ alkyl, unsubstituted phenyl, and substituted phenyl.

6. The electrochromic device of claim 4, wherein said cathodic component further comprises counter-anions, wherein each counter-anion of the cathodic component is independently selected from the group consisting of $BF_4^-$, $PF_6^-$, $ClO_4^-$, $CF_3SO_3^-$ or $(CF_3SO_2)_2N^-$ and $(CF_3SO_2)_3C^-$.

7. The electrochromic device of claim 1, wherein said electrolyte comprises,
at least one electrolyte anion, wherein each electrolyte anion is independently selected from bis(perfluoro(linear or branched $C_1$-$C_6$ alkysulfonyl)imide, and
at least one electrolyte cation, wherein each electrolyte cation is independently selected from 1-(linear or branched $C_1$-$C_6$ alkyl)-3-(linear or branched $C_1$-$C_6$ alkyl)imidazolium, or 1-(linear or branched $C_1$-$C_6$ alkyl)-1-(linear or branched $C_1$-$C_6$ alkyl)piperidinium.

8. The electrochromic device of claim 1, wherein said polymer matrix comprises a polymer, wherein said polymer comprises at least one of poly((meth)acrylonitrile), poly(vinylidene fluoride), poly(vinylidene fluoride-co-perfluoro (linear or branched $C_1$-$C_6$ alkylene)), or poly((linear or branched $C_1$-$C_8$ alkyl)(meth)acrylate).

9. The electrochromic device of claim 1 wherein,
said cathodic component is present in an amount of from 0.8 percent by weight to 6.25 percent by weight,
said anodic component is present in an amount of from 0.8 percent by weight to 6.25 percent by weight,
said electrolyte is present in an amount of from 16.4 percent by weight to 25.0 percent by weight, and
said polymer matrix is present in an amount of from 62.5 percent by weight to 82.0 percent by weight,
the percent weights in each case being based on total weight of said cathodic component, said anodic component, said electrolyte, and said polymer matrix.

10. An electrochromic composition comprising,
(i) a cathodic component,
(ii) an anodic component,
(iii) an electrolyte,
(iv) a polymeric thickener, and
(v) a solvent,
wherein said anodic component comprises an anodically-coloring electrochromic compound represented by the following Formula (I),

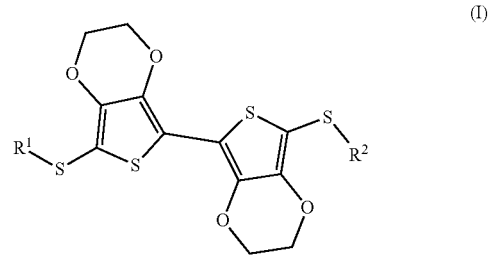
(I)

wherein R¹ and R² are each independently selected from linear or branched $C_3$-$C_{20}$ alkyl.

11. The electrochromic composition of claim 10, wherein R¹ and R² are each independently $C_3$-$C_{10}$ alkyl.

12. The electrochromic composition of claim 11, wherein R¹ and R² are each independently linear or branched $C_4$-$C_8$ alkyl.

13. The electrochromic composition of claim 10, wherein said cathodic component comprises a 1,1'-disubstituted-4,4'-dipyridinium cation represented by the following Formula (II),

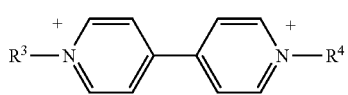
(II)

wherein R³ and R⁴ are each independently selected from linear or branched $C_1$-$C_{10}$ alkyl, unsubstituted aryl, and substituted aryl.

14. The electrochromic composition of claim 13, wherein R³ and R⁴ are each independently selected from linear or branched $C_1$-$C_4$ alkyl, unsubstituted phenyl, and substituted phenyl.

15. The electrochromic composition of claim 13 wherein, said cathodic component further comprises counter-anions, wherein each counter-anion of the cathodic component is selected from the group consisting of $BF_4^-$, $PF_6^-$, $ClO_4^-$, $CF_3SO_3^-$ or $(CF_3SO_2)_2N^-$ and $(CF_3SO_2)_3C^-$.

16. The electrochromic composition of claim 10, wherein said electrolyte comprises,
at least one electrolyte anion, wherein each electrolyte anion is independently selected from bis(perfluoro(linear or branched $C_1$-$C_6$ alkysulfonyl)imide, and
at least one electrolyte cation, wherein each electrolyte cation is independently selected from 1-(linear or branched $C_1$-$C_6$ alkyl)-3-(linear or branched $C_1$-$C_6$ alkyl)imidazolium, or 1-(linear or branched $C_1$-$C_6$ alkyl)-1-(linear or branched $C_1$-$C_6$ alkyl)piperidinium.

17. The electrochromic composition of claim 10, wherein said polymeric thickener comprises a polymer, wherein said polymer comprises at least one of poly((meth)acrylonitrile), poly(vinylidene fluoride), poly(vinylidene fluoride-co-perfluoro(linear or branched $C_1$-$C_6$ alkylene)), or poly((linear or branched $C_1$-$C_8$ alkyl)(meth)acrylate).

18. The electrochromic composition of claim 10, wherein said solvent comprises at least one of ethylene carbonate, propylene carbonate, gamma-butyrolactone, gamma-valerolactone, N-methylpyrrolidone, polyethylene glycol, or carboxylic acid esters of polyethylene glycol.

19. The electrochromic composition of claim 10 wherein, said cathodic component is present in an amount of from 0.2 percent by weight to 3.6 percent by weight, said anodic component is present in an amount of from 0.2 percent by weight to 3.6 percent by weight,
said electrolyte is present in an amount of from 3.8 percent by weight to 14.3 percent by weight,
said polymeric thickener is present in an amount of from 19.2 percent by weight to 35.7 percent by weight, and
said solvent is present in an amount of from 42.8 percent by weight to 76.6 percent by weight,
the percent weights in each case being based on total weight of said cathodic component, said anodic component, said electrolyte, said polymeric thickener, and said solvent.

* * * * *